United States Patent
Wiesel

(10) Patent No.: US 6,343,932 B1
(45) Date of Patent: Feb. 5, 2002

(54) DELIVERY SYSTEM FOR WHITENING TEETH

(76) Inventor: Peter E. Wiesel, 222 New Rd., Central Park East, Suite 401, Linwood, NJ (US) 08221

( * ) Notice: Subject to any disclaimer, the term of this patent is extended or adjusted under 35 U.S.C. 154(b) by 0 days.

(21) Appl. No.: 09/711,027

(22) Filed: Nov. 13, 2000

(51) Int. Cl.[7] .............................. A61C 5/00; A61K 6/02
(52) U.S. Cl. ......................... 433/215; 433/80; 424/435
(58) Field of Search .......................... 433/80, 215, 216; 424/401, 435, 49, 53

(56) References Cited

U.S. PATENT DOCUMENTS

| | | | |
|---|---|---|---|
| 3,688,406 A | * | 9/1972 | Porter et al. |
| 4,428,373 A | | 1/1984 | Seid et al. |
| 4,496,322 A | | 1/1985 | Sandham et al. |
| 4,990,089 A | | 2/1991 | Munro |
| 5,032,178 A | | 7/1991 | Cornell |
| 5,032,445 A | | 7/1991 | Scantlebury et al. |
| 5,098,303 A | | 3/1992 | Fischer |
| 5,122,056 A | | 6/1992 | Barbee |
| 5,240,415 A | | 8/1993 | Haynie |
| 5,326,685 A | | 7/1994 | Gaglio et al. |
| 5,340,581 A | * | 8/1994 | Tseng et al. ................. 424/401 |
| 5,571,502 A | | 11/1996 | Winston et al. |
| 5,575,654 A | | 11/1996 | Fontenot |
| 5,603,922 A | | 2/1997 | Winston et al. |
| 5,605,675 A | | 2/1997 | Usen et al. |
| 5,616,140 A | | 4/1997 | Prescott |
| 5,645,428 A | | 7/1997 | Yarborough |
| 5,707,235 A | * | 1/1998 | Knutson ..................... 433/213 |
| 5,713,738 A | | 2/1998 | Yarborough |
| 5,718,885 A | | 2/1998 | Gingold et al. |
| 5,766,011 A | | 6/1998 | Sibner |
| 5,785,527 A | | 7/1998 | Jensen et al. |
| 5,817,296 A | | 10/1998 | Winston et al. |
| 5,833,957 A | | 11/1998 | Winston et al. |
| 5,858,333 A | | 1/1999 | Winston et al. |
| 5,891,453 A | | 4/1999 | Sagel et al. |
| 5,894,017 A | | 4/1999 | Sagel et al. |
| 5,895,641 A | | 4/1999 | Usen et al. |
| 6,045,811 A | | 4/2000 | Dirksing et al. |
| 6,096,328 A | * | 8/2000 | Sagel et al. ................. 424/401 |
| 6,106,293 A | | 8/2000 | Wiesel |
| 6,136,297 A | * | 10/2000 | Sagel et al. ................... 424/49 |
| 6,155,832 A | | 12/2000 | Wiesel |
| 6,287,120 B1 | * | 9/2001 | Wiesel ....................... 433/215 |

* cited by examiner

Primary Examiner—Ralph A. Lewis
(74) Attorney, Agent, or Firm—Norman E. Lehrer

(57) ABSTRACT

A whitening system for a person's teeth includes a gel having a whitening agent, such as peroxide, contained therein. The gel is supported and carried in a channel formed in the central area of a strip of core material that also functions as a gum protective liner. The core and gum protective liner is preferably made of a biodegradable material or of a similar material that can be washed or brushed away. A release liner may be applied to the top of the combined gel and core and is removed to expose the gel when the system is to be used. Applied to the lower side of the core is a releasable backing layer that supports the gel and core and functions as an applicator for the system. The backing layer maintains the integrity of the core and allows the same to be molded to the surfaces of the teeth without having to directly handle the core with one's hands. To use the system, the release liner is removed and the core is fitted to the teeth with the gel in contact with the teeth and the gum protective liner covering the gum. Once the core has been fitted to the teeth, the backing layer is removed leaving the core in place with the gel and whitening agent remaining on the teeth. After a desired period of time, the core with the whitening gel is washed off, brushed off, pulled off, or is allowed to simply dissolve.

5 Claims, 1 Drawing Sheet

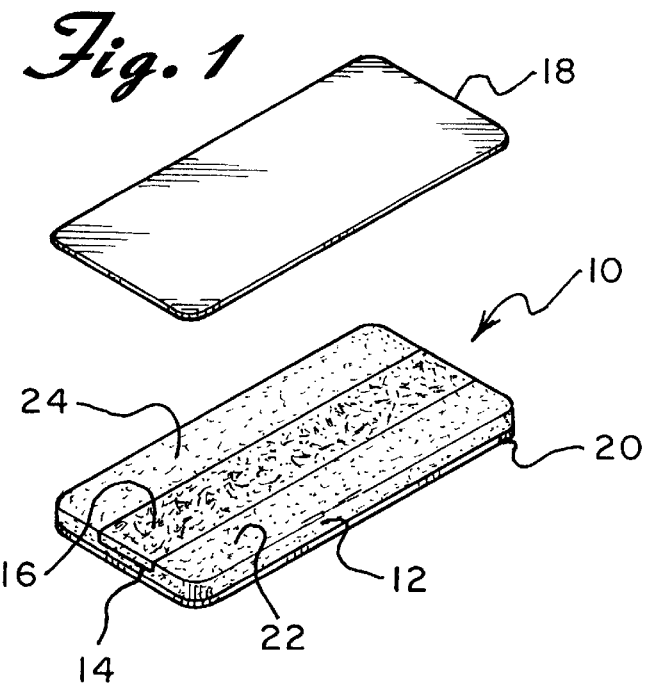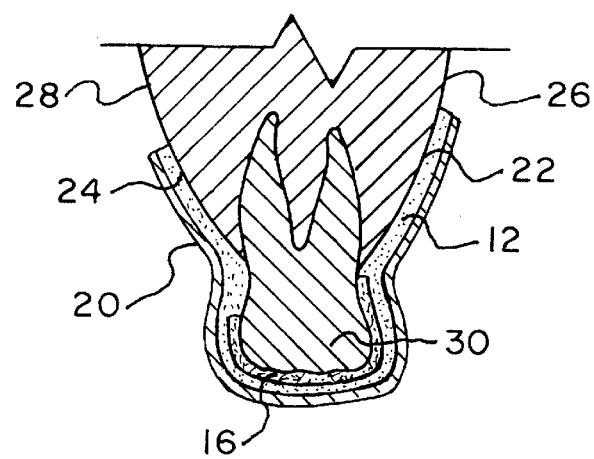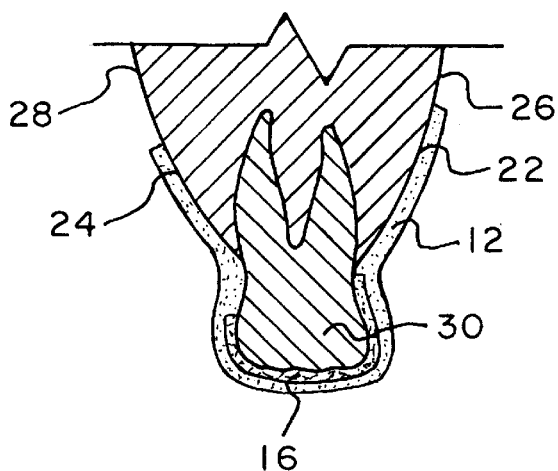

DELIVERY SYSTEM FOR WHITENING TEETH

BACKGROUND OF THE INVENTION

The present invention is directed toward a delivery system for whitening teeth and more particularly, toward a system which delivers a whitening agent to a person's teeth and which is easy to use, effective and inconspicuous.

Dentists, like other health care professionals, often seek ways in which to improve instruments and procedures in order to provide better care for their patients. For example, dentists have experimented with various procedures for whitening teeth. One such procedure involves dipping a gauze strip into a bleaching material, applying the strip to a patient's tooth, and then exposing the covered tooth to a light source. This procedure, however, is not very effective because the amount of light which passes through the gauze strip is minimal since it is not transparent. A further limitation of this procedure is that because only one tooth is whitened at a time, the procedure is time-consuming, thereby increasing the patient's discomfort and exposure to the light source.

Currently, dentists whiten a patient's teeth by preparing a peroxide solution and coating the teeth with the solution. Once the solution is placed on the teeth, the teeth are exposed to a heat lamp or a laser light in order to heat the peroxide and to accelerate the bleaching process. In order to protect the patient's gums, a rubber sheet, Vaseline, or a light cured gel may be placed on the gums.

There are several disadvantages with the above-described process. For example, the rubber sheet placed over the patient's gums may stretch so that the peroxide solution leaks around the rubber sheet, exposing the patient's gums to the peroxide, thereby causing the patient discomfort. Also, this method cannot be performed on the upper set of teeth and the lower set of teeth simultaneously. Rather, only one set of teeth may be whitened at a time. Another disadvantage is that if a heat lamp is used a substantial amount of time is required in order to effectively bleach the teeth. Thus, the patient is exposed to the lamp for a great deal of time. This can cause extreme discomfort and inconvenience to the patient. Furthermore, the peroxide solution often times cannot be concentrated on the teeth. That is, the solution may drip off of the teeth if too much of the solution is applied or the solution may dry out if too little of the solution is applied.

Another method of whitening teeth is disclosed in U.S. Pat. No. 5,645,428 to Yarborough. This patent discloses using a laser light to activate bleaching agents applied to a patient's teeth. A mixture of peroxide and a first catalyst is prepared and then applied to the teeth. The teeth are then exposed to a laser light which activates the peroxide and catalyst to accelerate the bleaching process without heat. A second mixture of peroxide and a catalyst is then prepared and applied to the teeth. Again, the teeth are exposed to a laser light which heat activates the second mixture to accelerate the bleaching process. This process, however, increases the patient's exposure to laser light.

In yet another system, a peroxide solution may be combined with a gel which acts as a carrier. The mixture is then applied to a person's teeth which are then exposed to a light source. This system may be used by a person without the aid of a dentist or other medical personnel. That is, the peroxide-gel solution may be placed within a plastic mouthguard, such as shown in U.S. Pat. No. 4,990,089 to Munro, which is worn by a person overnight. A problem with this system is that the peroxide-gel solution decreases the effectiveness of the peroxide because generally these solutions are weak.

Also, the use of gel, in any dental office system, decreases the effectiveness of the peroxide because of the gel's opacity. That is, light is not able to pass through to all of the peroxide because of the opacity of the gel. Also, the gel prevents full contact of the tooth with the peroxide solution, thereby decreasing the effectiveness of the peroxide solution.

U. S. Pat. No. 6,106,293 issued to Wiesel, one of the current inventors, describes a system for whitening teeth that is intended to be used in a dentist's office and which is much more effective than previously known systems. The Wiesel patented system uses a transparent carrier for holding a peroxide solution in contact with a person's teeth. A laser or other light can then be applied to increase the whitening effect.

An even more effective whitening technique is disclosed in allowed U.S. application Ser. No. 09/414,183 also filed by Wiesel. This system uses a flexible porous material as the carrier for the whitening solution. The porous material becomes at least translucent when it is wetted by the whitening solution so that the teeth and solution can be exposed to light through the carrier to increase the whitening effect. The porous carrier also allows additional whitening solution to be applied to the teeth while the system is in place on the patient's teeth. This is accomplished by brushing additional whitening solution onto the outer exposed surface of the carrier and allowing the same to be wicked into the inner surface to contact the teeth. While the Wiesel systems are effective, they are intended for use in a dentist's office.

A home system for whitening teeth is disclosed in U. S. Pat. No. 5,891,453 to Sagel et al. The delivery system described in this patent comprises a strip of flexible material onto which the user may place a quantity of a tooth whitening substance. The flexible strip along with the tooth whitening substance is then placed on the surface of the teeth and is allowed to remain in place for a sufficient period of time to allow the active ingredient within the substance to act on the surface of the teeth. Because the system described in this patent is intended for home use, the concentration of the whitening substance must be relatively low and there is no suggestion of applying ultraviolet light or any other light in order to enhance the whitening function.

A similar home system for treating teeth is disclosed in U.S. Pat. No. 6,045,811 to Dirksing et al. This patented system utilizes a carrier strip in the form of a permanently deformable material that carries an oral care substance thereon and which holds the same in place on the teeth by conforming to the shape thereof. The carrier strip, however, must remain in place as long as the oral care substance is being applied and is, therefore, normally visible to others. Since the substance must be maintained against the teeth for substantial periods of time, patients may hesitate to use such devices even in their own homes.

There is, therefore, a need in the art for a home whitening system that is effective, easy to use and less conspicuous than the prior art systems that are now available.

SUMMARY OF THE INVENTION

The present invention is designed to overcome the deficiencies of the prior art discussed above. It is an object of the present invention to provide a delivery system for whitening a person's teeth that is convenient to use.

It is a further object of the present invention to provide a delivery system for whitening a person's teeth which remains on the teeth without the aid of a carrier or other type of support means so as to be less obvious to others.

It is a still further object of the present invention to provide a delivery system for whitening a person's teeth which can be used by a person at home but which is still effective in achieving whitening results.

In accordance with the illustrative embodiments demonstrating features and advantages of the present invention, there is provided a whitening delivery system for a person's teeth that includes a gel having a whitening agent, such as peroxide, contained therein. The gel is supported and carried in a channel formed in the central area of a strip of core material that also functions as a gum protective liner. The core and gum protective liner is preferably made of a biodegradable material or of a similar material that can be washed or brushed away. A release liner may be applied to the top of the combined gel and core and is removed to expose the gel when the system is to be used. Applied to the lower surface of the core is a releasable backing layer that supports the gel and core and functions as an applicator for the system. The backing layer maintains the integrity of the core and allows the same to be molded to the surfaces of the teeth without having to directly handle the core with one's hands. To use the system, the release liner is removed and the core is fitted to the teeth with the gel in contact with the teeth and the gum protective liner covering the gum. Once the core has been fitted to the teeth, the backing layer is removed leaving the core in place with the gel and whitening agent remaining on the teeth. After a desired period of time, the core with the whitening gel is washed off, brushed off, pulled off, or is allowed to simply dissolve.

Other objects, features, and advantages of the present invention will be readily apparent from the following detailed description of a preferred embodiment.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

FIG. 1 is a partially exploded perspective view of a delivery system for whitening teeth in accordance with the present invention;

FIG. 2 is a schematic representation of the system initially applied to a person's teeth, and FIG. 3 is a view similar to FIG. 2 with the lower or outer backing layer removed.

DETAILED DESCRIPTION OF THE PREFERRED EMBODIMENT

Referring now to the drawings in detail wherein like reference numerals have been used throughout the various figures to designate like elements, there is shown in FIG. 1 a delivery system for whitening teeth constructed in accordance with the principles of the present invention and designated generally as 10.

The invention essentially includes an elongated thin flexible core 12. Although the core 12 is shown as having a definite length, it could be produce in an indefinite length such as on a roll or the like and then cut to the proper length as needed. The length selected could be either enough to cover one or two adjoining teeth or all of a person's teeth.

The core 12 is preferably made of a degradable material or of a similar material that can be washed or brushed away. For reasons that will become apparent, it should also be a material that is innocuous to a person's gums and other tissue within the mouth when contacting the same. The core 12 may be made from a medical grade silicone (LSR 30 or 40), a medical grade acrylic such as carbopol resins or cellulose products such as carboxy methyl, ethyl, carboxymethyl amalose or hydroxy methyl or ethyl cellulose polyisobutyrate or combinations of these various products.

In the preferred embodiment, the core 12 is comprised of a 0.5% celluose and 0.1% carbopol (acrylic polymer) solution that is freeze dried. Preferably the celluose is comprised of sodium carboxymethylcelluose, Hercules 7MF PH. The carbopol is preferred to be comprised of BF Goodrich 1320 or 981 P NF grade material. The solution is compounded using purified water and sodium hydroxide as a neutralizer. The freeze dried material is a solid sheet and is flexible and adherent to the teeth and gum-line. The residual moisture of the sheet may be measured through lose on drying and would not exceed 11%.

The core provides some structural support but is also somewhat viscous and tacky. The core or carrier 12 may be formulated so as to be transparent, translucent or opaque depending on whether it may be desired to enhance the whitener that is to be used through the use of light activation.

A recess or channel 14 or the like is formed at the center of the core 12 and extends substantially the entire length of the core. The width of the channel 14 is preferably of sufficient dimension to cover the height of a person's teeth. It could, however, be somewhat wider since, when applied, the excess width will simply be folded over and will engage the back of the person's teeth as will be clearer hereinafter.

A bead or thin layer of a gel 16 fills the channel 14 in the core 12. This can be accomplished either by pouring the gel therein or by utilizing a knife over roller, doctor blade or substantially any other known process. The gel 16 carries the whitening agent such as peroxide and should be somewhat tacky so as to adhere both to the core 12 and to a person's teeth.

The gel 16 is preferably comprised of a 0.5% carbopol (acrylic polymer), BF Goodrich 1320 or 981 P NF grade and is formulated with purified water and sodium hydroxide so as to have a viscosity of approximately 60,000 cps. The gel 16 is activated and constitutes a whitening agent with the addition of 30 to 35% hydrogen per oxide.

In the preferred embodiment, the gel 16 is prearranged in the channel 14 prior to packaging. However, it is also possible to supply the core 12 without the gel 16 prepackaged therein and to provide a separate tube of the gel 16 whitening agent to be applied by the user. This alternative arrangement would maximize the potency of the whitening agent.

A release liner 18 overlies the top of the combined gel 16 and core 12 in order to protect the same during storage. This release liner may be comprised of paper or plastic or the like and is designed so as not to adhere well to the gel 16 or the core material 12. The release liner 18 is, of course, removed before the delivery system 10 is utilized.

Located beneath or on the reverse side of the core 12 is a backing layer 20. The backing layer 20 supports the core and the gel carried thereon but is somewhat flexible and also is designed so as to not adhere well to the core 12. The flexible backing layer 20 may be made of paper, foam (either open or closed cell), woven or non-woven fabric, polyolefin, copolyester, polyester, polyurethane, ethyl vinyl acetate, polyether block amides, ethylene methacrylic acid or polypropylene. The preferred form of the backing layer 20 is a 30 mil film of polyolefin with a light 30K silicone oil coating. The film is flexible and the silicone oil allows temporary adherence to the core 12 for treatment application as indicated below.

As will be seen, the backing layer 20 maintains the integrity of the core and gel 16 as the same is molded onto a person's teeth and gums but can easily be removed therefrom while leaving the core in place.

The teeth whitening delivery system 10 described above is utilized in the following manner. First, a length of the delivery system is obtained. Again, this can be done either by having them precut into predetermined lengths or by providing a continuous roll and the user cutting a desired amount from the roll. Thereafter, the release liner 18 is removed to thereby expose the upper surface of the core 12 and the gel 16.

With the release liner 18 removed, the user molds the core 12 around his or her teeth 30 with the gel whitener in contact with the outer surface of the teeth being treated. As shown in FIG. 3, the gel 16 can also extend around to the inner surface of the teeth but this is not absolutely necessary. When the core 12 is molded about the teeth, the surfaces 22 and 24 thereof overlie the surfaces 26 and 28 of a person's gum on the inside and outside of their jaw as shown in FIGS. 2 and 3.

The backing layer 20 is utilized to help mold the delivery system into place. That is, a person, using his or her fingers, presses the delivery system 10 against the teeth and gums with the gel 16 being in contact with the teeth as pointed out above. The use of the backing layer 20 prevents the person's fingers from coming into direct contact with the core 12. This maintains the integrity of the core as it is being molded into place. After the core is in the proper position as shown in FIG. 2, the backing layer 20 is peeled away. The viscosity and tackiness of the core 12 and gel 16 are selected so that the backing layer 20 can be easily removed therefrom while the core 12 and gel 16 remain in place as shown in FIG. 3.

With the backing layer 20 removed, the teeth whitening system 10 can then remain in the person's mouth for any desired period of time. Thereafter, it can be removed by brushing, rinsing or peeling depending on the material chosen for the core 12.

As should readily apparent to those skilled in the art, because the gel 16 contacts only the tooth surface and does not contact the gums, the strength of the peroxide or other whitening material therein can be stronger than may normally be utilized in a home delivery system. The core 12 overlying the gums protects the same. Similarly, the exposed under surface of the core 12 which may come into contact with the person's tongue, lips and cheeks or other parts of the mouth also protects them from the gel. The core 12, as pointed out above, is made from a material which is essentially innocuous to a person's gums and other portions of the mouth when coming into contact therewith.

Although the invention has been described in connection with a system for whitening teeth, it must be understood that this is merely the preferred embodiment. It should be readily apparent to those skilled in the art that the invention could be used for otherwise treating the teeth. For example, a desensitizing agent or substantially any other substance or medicament could be applied using the invention. This can be accomplished simply by substituting the desensitizing agent or other material for the whitening agent in the gel.

The present invention may be embodied in other specific forms without departing from the spirit or essential attributes thereof and accordingly, reference should be made to the appended claims rather than to the foregoing specification as indicating the scope of the invention.

I claim:

1. A system for treating teeth comprising:

an elongated core having an upper surface and a lower surface, said core being comprised of a thin flexible strip of degradable material and having a central portion extending substantially the entire length of said strip, the material forming said core being essentially innocuous to a person's gums when placed in contact therewith;

a gel carried by the upper surface of said core in at least said central portion thereof, said gel including a composition for treating the teeth;

a releasable flexible backing layer on the lower surface of said core for supporting the core and gel carried thereon, said backing layer maintaining the integrity of the core when the core and gel are molded onto a person's teeth and gums but being removable from said core after the core is applied to the teeth and gums while leaving the core in place.

2. The system as claimed in claim 1 further including a release liner applied to the top of the combined gel and core and removable to expose the gel when it is desired to utilize the system.

3. The system as claimed in claim 1 wherein said central portion of said core includes a channel extending substantially the entire length of said strip and wherein said gel is within said channel.

4. The system as claimed in claim 1 wherein said gel includes a whitening agent.

5. The system as claimed in claim 1 wherein said gel includes a desensitizing agent.

* * * * *